United States Patent [19]

Albisser et al.

[11] 4,423,039
[45] Dec. 27, 1983

[54] DISAGGREGATED SOLUTIONS OF POLYPEPTIDES, THEIR PREPARATION AND USE

[75] Inventors: A. Michael Albisser; William D. Lougheed, both of Toronto, Canada

[73] Assignee: The Hospital for Sick Children, Toronto, Canada

[21] Appl. No.: 254,823

[22] Filed: Apr. 16, 1981

Related U.S. Application Data

[63] Continuation of Ser. No. 147,444, May 7, 1980, abandoned.

[30] Foreign Application Priority Data

Feb. 29, 1980 [CA] Canada ................................ 346684

[51] Int. Cl.³ .................... A61K 37/26; C07C 103/52; C07G 7/00
[52] U.S. Cl. ............................. 424/178; 260/112.5 R; 260/112.7; 424/177
[58] Field of Search .............................. 424/178, 177; 260/112.7, 112.5 R

[56] References Cited

U.S. PATENT DOCUMENTS

| 2,474,729 | 6/1949 | Durel et al. | 424/178 |
| 2,902,408 | 9/1959 | Bouman et al. | 424/178 |
| 3,014,842 | 12/1961 | Schlichtkrull | 424/178 |
| 3,584,121 | 6/1971 | Krayenbuhl et al. | 424/178 |
| 3,715,345 | 2/1973 | Smith | 424/178 |
| 4,183,849 | 1/1980 | Hansen et al. | 424/178 |

FOREIGN PATENT DOCUMENTS 570237  2/1979  Belgium .............................. 424/178

OTHER PUBLICATIONS

*Diabetes* vol. 28, Mar. 1979, 196-203.
Glucagon for Injection, USP–Jan. 1979, PA 9643 CCAP, Eli Lilly and Company (Canada) Ltd.

*Primary Examiner*—Frederick E. Waddell
*Attorney, Agent, or Firm*—Rogers, Bereskin & Parr

[57] ABSTRACT

The present invention is directed to a solution of a polypeptide, such as, for example, insulin, the solution being prepared and maintained at pH 6.8 to 8.0 and in which the polypeptide remains in solution in disaggregated form. This is accomplished by the use of the bicarbonate ion in the solution, the bicarbonate ion being present in a concentration of 2 mmolar to 2.5 molar.

A method for preparing the polypeptide solution and the use of the solution in maintaining normoglycemia are provided.

12 Claims, No Drawings

DISAGGREGATED SOLUTIONS OF POLYPEPTIDES, THEIR PREPARATION AND USE

This is a continuation of application Ser. No. 147,444, filed May 7, 1980, now abandoned.

This invention relates to an aqueous solution of pH 6.8 to 8.0 containing a polypeptide such as insulin or glucagon in disaggregated form and containing the bicarbonate ion.

It is well known that subcutaneous insulin injections fail to normalize most of the metabolic derangements of diabetes mellitus. In contrast, it has been found in recent years that insulin which is infused by either closed-loop or open-loop insulin delivery mechanisms remarkably improves many of the abnormalities, even after short term application. Closed-loop systems regulate insulin delivery on the basis of continuously measured blood glucose concentrations while open-loop systems regulate insulin delivery according to a carefully selected schedule usually involving a basal infusion rate which is augmented at mealtime. Almost complete metabolic and hormonal normalization can be achieved with pre-programmed intra-portal insulin delivery.

The further development of an implantable artificial endocrine pancreas has been prevented by the propensity for insulin solutions to precipitate and/or gradually aggregate in the reservoirs of the open-loop systems. Such aggregates interfere with the flow of insulin and eventually result in clinically unacceptable blood glucose control, regardless of the pH of the insulin being administered.

It has been found that good glucose control has been achieved only when the reservoirs and delivery components of these systems have been replaced every one to three days. Otherwise a tendency to unacceptable hyperglycemia prevailed.

Microscopic examination of the obstructions formed in the delivery systems revealed amorphous and crystalline structures which subsequent analysis proved to be highly concentrated with immunoreactive insulin. Similar optical examination of the solutions contained in the reservoir, illuminated with polarized light, showed suspensions of crystalline and amorphous aggregates of insulin. The size of these aggregates increased with time and eventually these accumulated and obstructed the entrances of the small catheters used to convey the insulin from the pumps to the subjects. This rapidly resulted in hyperglycemia which could not be reversed by increasing the pumping rate because the flow path was obstructed by the accumulation of aggregates and there was a risk of hypoglycemia if the obstructions were dislodged by the increased pressure generated by the pump. Normoglycemia was restored by disconnecting the pump, flushing the tubes and replacing the reservoirs every 3 to 4 days.

A review of the literature reveals that many mechanisms or factors may be responsible for increasing the propensity of insulin to aggregate. Among these are abrupt changes of the flow path, motion, metal ion concentration, pH drop, etc. There is evidence that, although under appropriate conditions solutions of single component monomeric insulins can be formulated, these insulin solutions unless at extremely low, i.e. physiologic, concentrations will progressively aggregate starting within a few hours after storage regardless of the temperature of storage.

The conventional process for preparing neutral insulin solutions for physiological use involves dissolving the insulin in acidic sterile water at pH 2.5 to 2.9 and then adjusting the resultant solution to a pH of 7.0 to 7.5. When forming insulin solutions in this manner, the insulin must be brought through its isoelectric point, namely 5.3 to 5.4. It is thought that some irreversible aggregation will occur during this transition; the justification being that insulin is far less soluble at pH 7 to 7.5 than at pH 2.5 to 2.9. It is indeed for this very reason that commercial insulin is initially dissolved at acid rather than neutral pH.

It has now been found that it is possible to prepare a solution of insulin in which the insulin is far less aggregated with a larger portion in the monomeric state at pH 6.8 to 8.0, that is, at or near the physiological pH. Therefore the insulin is not brought through its isoelectric point following dissolution and this avoids any irreversible precipitation that might occur during the transition from acid to neutral pH.

It has also been found that another polypeptide namely glucagon which is not normally soluble in water at pH 6.8 to 8.0 can also be dissolved within this pH range. In general glucagon is stored in crystalline form and is dissolved immediately prior to subcutaneous or intravenous administration.

Therefore, the present invention is directed to neutral polypeptide solutions which have been prepared by a process which excludes the initial step of dissolving crystals in acidic or basic media.

Accordingly, the present invention provides an aqueous solution prepared at pH 6.8 to 8.0 containing a polypeptide selected from the group of insulin or glucagon in disaggregated form and containing the bicarbonate ion in a concentration of from 2 mmolar to 2.5 molar.

The insulin is generally present in the solution in an amount of 0.1 to 500 Units per ml of solution, with 1 to 100 Units being the preferred amount.

The bicarbonate ion can be added to the aqueous solution in the form of its salts, such as, for example, the alkali metal or ammonium salts thereof, or by increasing the partial pressure of carbon dioxide. It has also been found that in a suitably buffered solution it is possible to provide the necessary bicarbonate ions by using mammalian serum or a component of mammalian serum which has been separated from the serum by ultrafiltration to obtain the fraction having a molecular weight below 500 and then treating this fraction to obtain the component which is electronegatively charged at pH 7.

The serum which is useful for the preparation of the component containing the bicarbonate ion is the serum which is available from mammals, such as, for example, human serum, dog serum, pork serum or bovine serum. It will be appreciated that human and dog sera would not normally be used because of the difficulties encountered in obtaining them.

The process for the preparation of the component containing the bicarbonate ion normally involves obtaining the fresh serum from the blood of the animal by allowing the blood to clot and then removing the serum fraction after centrifugation. Although this serum fraction will suffice it is generally considered good practice to purify this fraction further.

To this end, the serum is then filtered in such a manner that only those substances having a molecular weight of less than 500 pass through. The low molecular weight product is then treated in such a manner that the negatively charged components are separated. This may be accomplished by passing the low molecular weight product through a positively charged gel at a pH of 7.0 to 7.5. The component containing the bicarbonate ion is bound to the gel in this manner. Subsequent washing of the gel at pH 2 to 4 allows collection of the extract containing the bicarbonate ions. This extract can then be used in the preparation of the desired insulin solutions. However, for physiological reasons, it may be desirable to further purify this low molecular weight extract and obtain a more specific product which can be used in the preparation of insulin solutions.

This can be done by gradient or stepwise pH elution of the electronegatively charged components of the crude extract. This may involve binding those components that are electronegatively charged at pH 7.5 to a positively charged gel and subsequently treating it in such a manner that those fractions which become unbound from the gel between pH 2.5 and 3.5 are collected.

Prior to the elution step, the low molecular weight extract may be treated further to purify and concentrate it, such as, for example, by being subjected to one or more ultra-centrifugation steps.

The preparation from serum of the component containing the bicarbonate ions will be better understood by reference to the following examples:

EXAMPLE 1

Fresh serum was filtered through an Amicon® porus filter which allowed only substances having a molecular weight of less than 500 to pass through. A low molecular weight eluent was collected. This low molecular weight eluent was then passed through a column packed with diethylaminoethyl cellulose (DEAE cellulose). The column was packed in the traditional manner. In order to protect the small peptides, 0.01 to 0.1 M 2-amino-2-hydroxymethyl-1,3-propanediol (hereafter referred to as Tris) in normal (0.9%) saline was used to suspend the gel in the column. The pH of the gel in the column was held between 7.0 and 7.5. The low molecular weight product was run through the column using 0.1 to 0.01 M Tris in normal (0.9%) saline as the hydrostatic head for the column. The components which were negatively charged at this pH were bound to the positively charged gel while all other constituents were eluted. The gel was then removed from the column and 0.01 M HCl was slowly added until the pH of the gel dropped to 2.5. This solution was then centrifuged at 25,000 g's for a minimum of 5 minutes. The supernatant was then pipetted off; the gel having been compacted into the bottom of the container during centrifugation. The supernatant extract was further purified by heating at 100° C. for 30 minutes in a closed container, followed by ultracentrifuging at 125,000 g's for 4 hours. The supernatant from the process at this point contained only the heat stable components of the serum that are less than 500 molecular weight and negatively charged at pH 7 to 7.5.

EXAMPLE 2

Example 1 was repeated and the supernatant obtained therefrom was further purified by gradient or stepwise pH elution in which the supernatant was bound once again to DEAE in a manner identical to that described in Example 1. Solutions of 0.1 M Tris in bacteriostatic water were then passed through the column. The pH was successively dropped, using hydrochloric acid, from 7.5 to 2.5 in intervals of 0.5 and each fraction was collected. Those fractions between 2.5 and 3.5 were then mixed. The pH of the mixture was raised to 7.5 using ammonium hydroxide. A concentrated relatively pure extract was then obtained.

Prior to carrying out the above examples, it is possible to quickly and easily remove the larger proteins and lipids prior to the ultrafiltration step and this enables the untrafiltration to be carried out approximately five times faster. In order to accomplish this, the whole serum is added to a 2:1 mixture of chloroform-methanol. This solution is mixed and allowed to settle for 15 minutes. The methanol which contains the desired fraction is pipetted off. Methanol and ethanol are then added to give a solution having an alcohol content between 40 and 70%. The solution is centrifuged at 25,000 g's for 10 minutes and the supernatant is pipetted off. The product can be used as the starting material for Example 1 or Example 2.

The same results can be achieved by slowly lowering the pH of whole serum from 7.5 to 2.5 and at intervals of 0.5 separating the precipitate from the supernatant (active portion) by centrifugation. Pooling of the supernatants then provides a solution which can be more quickly processed using the method outlined in Example 1.

The ability of the compounds capable of providing bicarbonate ions in solutions to dissolve insulin (and other polypeptides such as glucagon) has been determined by a simple reproducible assay which measures the dissolution times of zinc insulin crystals exposed to various aqueous solutions including solutions containing bicarbonate ions. The test involved transferring pork insulin crystals to a clean microscope slide using the tip of a 25 G needle so that 10 to 30 crystals were distributed in the field of view. A 25 $\mu$l aliquot of the test solution was pipetted to form a small droplet which covered the crystals. In most cases the crystals remained on the slide surface following the addition of the test solution. In those instances in which the crystals floated up into the solution the results were discarded as this enhanced the rate of dissolution. The pH's of the test solutions were measured and the former were adjusted where appropiate to pH 7.5 using 1 N NaOH or 1 N HCl.

Table 1 shows the dissolution times (expressed as the mean ±SEM) of various compounds at various concentrations.

TABLE 1

| Compound | | Dissolution Time ± SEM (Sec) | Concentration |
|---|---|---|---|
| Sodium | ⎫ | 50 ± 5 | 150 mmol/l |
| Sodium | | 360 ± 20 | 25 mmol/l |
| Potassium | Bicarbonate | " | " |
| Ammonium | (HCO$_3$—) | " | " |
| Lithium | ⎭ | " | " |
| Carbonic Acid | | " | " |
| Lactic Acid | ⎫ | >1200 | 150 mmol/l |
| Formic Acid | | >1200 | " |
| Sodium Pyruvate | | " | Physiologic |
| Taurine | | " | " |
| L-Proline | | " | " |
| Proline | | " | " |
| Cystine | | " | " |
| Cysteine | | " | " |
| L-Aspartic Acid | | " | " |
| L-Serine | Carboxyl | " | " |
| L-Threonine | End | " | " |

TABLE 1-continued

| Compound | Dissolution Time ± SEM (Sec) | Concentration |
|---|---|---|
| L-Glutamine | Terminal | " |
| L-Alanine | " | " |
| L-Methionine | " | " |
| L-Isoleucine | " | " |
| L-Leucine | " | " |
| Lysine | " | |
| Ornithine | " | " |
| Histidine | " | " |
| Human Serum (Fasting) | 212 ± 7 | " |
| Urea | 20% at 300 sec | 25 mmol/l |
| Distilled H₂O | Nil at 1800 sec | |
| Ringer's Lactate | Nil at 1800 sec | undiluted |
| Normal Saline | Nil at 1800 sec | 0.9% NaCl |

Similar assays were carried out with the component containing bicarbonate ions which was obtained from serum. In all cases the zinc insulin crystals dissolved in 1 to 3 minutes. All highly purified serum components obtained following the procedure of Example 2 had faster dissolution times of 40 to 50 seconds.

The polypeptide glucagon was tested as above using the purified component from serum containing the bicarbonate ions. All crystals dissolved in 120 to 140 seconds. A 150 mmol solution of sodium bicarbonate (pH 7.5) in distilled water dissolved the glucagon in 45±12 seconds. However, no dissolution was observed after 30 minutes in distilled water, Ringer's lactate, normal saline or 5% human serum albumin in normal saline, all at pH 7.5.

The addition of 1 to 1.5% of the serum fraction to the insulin solutions has allowed to date 270 days of continuous infusion. No plugging of the delivery systems has occured. The solution in the reservoir has been regularly examined under 400× magnification and no insulin aggregates have been observed. Previous to the implementation of the use of the serum fraction, aggregation was observed by the 3rd or 4th day.

The addition of 0.1 g of clean etched copper to 10 ml of 5 U/ml neutral insulin solutions causes severe visible aggregation within 4 hours. Both motion and elevated temperatures (37° C.) severely accelerate the process. At 37° C. shaking of insulin solutions containing 0.01 g/ml copper is thus an excellent method for testing the "anti-aggregation" effect of any additive. To this end sodium bicarbonate solutions having concentrations of 2.5, 25, 250 and 2,500 mmolar were prepared. Biostatic water was used as the diluent. Neutral pork insulin was added to each to give a final concentration of 5 U/ml. To each sterile 10 ml vial 0.1 g of copper was added. Control vials were prepared exactly as above but no bicarbonate was added. The vials were aggitated on an Eberback shaker at 37° C. The experiment was run in triplicate at pH 7.5. All control vials showed severe aggregation after 4 hours. To date all vials containing bicarbonate have remained clear for 35 days.

The embodiments of the invention in which an exclusive property or privilege is claimed are defined as follows:

1. A process for the preparation of an aqueous polypeptide solution having a pH in the range of 6.8 to 8.0, wherein said polypeptide is selected from the group consisting of insulin and glucagon, said process comprising dissolving the polypeptide and a sufficient amount of bicarbonate ion in water to obtain an aqueous solution containing polypeptide in disaggregated form and bicarbonate ion in a concentration of 2 mmolar to 2.5 mmolar; and maintaining the resulting solution during its formation at a pH above the isoelectric point of the polypeptide in aqueous solution;

wherein the bicarbonate ion increases the rate of dissolution of the polypeptide in the water and maintains the polypeptide in disaggregated form in the solution.

2. A process as claimed in claim 1 in which the bicarbonate is introduced into the water by the addition of an alkali metal or ammonium salt thereto.

3. A process as claimed in claim 1 in which the bicarbonate ion is introduced into the water by means of carbon dioxide.

4. A process as claimed in claim 1 in which the polypeptide is insulin and the insulin is present in the solution in an amount comprising 0.1 to 500 Units of insulin per ml of solution.

5. A process as claimed in claim 1 in which the polypeptide is insulin and the insulin is present in the solution in an amount comprising 1.0 to 100 Units of insulin per ml of solution.

6. In an improved method of maintaining substantially normoglycemia in a mammal by injecting into the mammal a glycemia normalizing amount of an aqueous polypeptide solution from an open loop or closed loop polypeptide delivery system, the improvement wherein said solution is an aqueous polypeptide solution having a pH in the range of 6.8 to 8.0 comprising water having dissolved therein in disaggregated form a polypeptide selected from the group consisting of insulin and glucagon, wherein said solution has been maintained during its formation at a pH above the isoelectric point of said polypeptide in aqueous solution; and wherein said solution also contains bicarbonate ion in an amount of 2 mmolar to 2.5 molar to increase the rate of dissolution of the polypeptide in the water and to maintain the polypeptide in disaggregated form in the solution.

7. A method as claimed in claim 6 in which the polypeptide is insulin and the insulin is present in an amount comprising 0.1 to 500 Units of insulin per ml of solution.

8. A method as claimed in claim 6 in which the polypeptide is glucagon.

9. A method as claimed in claim 7 in which the bicarbonate ion is introduced into the solution by the addition to the solution of components of mammalian serum having a molecular weight below 500.

10. A method as claimed in claim 7 in which the insulin is present in an amount comprising 1 to 100 Units of insulin per ml of solution.

11. A method as claimed in claim 6 in which the bicarbonate is introduced into the water by the addition of an alkali metal or ammonium salt thereto.

12. A method as claimed in claim 6 in which the bicarbonate ion is introduced into the water by means of carbon dioxide.

* * * * *